United States Patent [19]
Mond et al.

[11] Patent Number: 5,874,085
[45] Date of Patent: Feb. 23, 1999

[54] VACCINE FOR ENHANCED PRODUCTION OF IGA ANTIBODIES

[75] Inventors: James J. Mond, Jerusalem, Israel; Clifford M. Snapper, Potomac, Md.

[73] Assignee: Henry M. Jackson Foundation for the Advancement of Military Medicine, Rockville, Md.

[21] Appl. No.: 400,322

[22] Filed: Mar. 8, 1995

Related U.S. Application Data

[63] Continuation-in-part of Ser. No. 315,492, Sep. 30, 1994, abandoned, which is a continuation-in-part of Ser. No. 150,510, Nov. 10, 1993.

[51] Int. Cl.[6] .......................... A61K 39/00; A61K 38/18; A61K 38/19; A61K 39/02
[52] U.S. Cl. ..................... 424/195.11; 424/184.1; 424/193.1; 424/194.1; 424/278.1; 424/85.2; 424/85.4; 424/197.11
[58] Field of Search .............................. 424/184.1, 278.4, 424/193.1, 85.2; 514/2, 8, 885

[56] References Cited

U.S. PATENT DOCUMENTS

| | | | |
|---|---|---|---|
| 5,231,168 | 7/1993 | Dziegel et al. | 530/350 |
| 5,371,197 | 12/1994 | Marburg et al. | 530/404 |
| 5,456,914 | 10/1995 | Stine et al. | |
| 5,585,100 | 12/1996 | Mond et al. | |

FOREIGN PATENT DOCUMENTS

| | | |
|---|---|---|
| 0585943 | 3/1994 | European Pat. Off. |
| WO 90/14104 | 11/1990 | WIPO |
| WO 91/01146 | 2/1991 | WIPO |

OTHER PUBLICATIONS

T. McIntyre et al., Novel In Vitro Model for High–Rate IgA Class Switching, The Journal Of Immunology, vol. 154, No. 7, pp. 3156–3161, Apr. 1, 1995.
M. Brunswick et al., Picogram Quantities of Anti–Ig Antibodies Coupled to Dextran Induce B Cell Proliferation, The Journal of Immunology, vol. 140, No. 10, pp. 3364–3372, May 15, 1988.
P. Kim et al., Tranforming Growth Factor $\beta 1$ Increases IgA Isotype Switching at the Clonal Level, The Journal of Immunology, vol. 145, No. 11, pp. 3773–3778, Dec. 1, 1990.
P. Shockett et al., Effect of Cytokines on Switching to IgA and $\alpha$ Germline Transcripts in the B Lymphoma I.29$\mu$, The Journal of Immunology, vol. 147, No. 12, pp. 4374–4383, Dec. 15, 1991.
R. Ehrhardt et al., Effect of Transforming Growth Factor (TGF)–$\beta 1$ on IgA Isotype Expression, The Journal of Immunology, vol. 148, No. 12, pp. 3830–3836, Jun. 15, 1992.
C. Snapper et al., IgE Class Switching is Critically Dependent Upon the Nature of the B Cell Activator, In Addition to the Presence of IL–4, The Journal of Immunology, vol. 147, No. 4, pp. 1163–1170, Aug. 15, 1991.
C. Snapper et al., Multivalent, but not Divalent, Antigen Receptor Cross–Linkers Synergize with CD40 Ligand for Induction to Ig Synthesis and Class Switching in Normal Murine B Cells, The Journal of Immunology, vol. 154, No. 3, pp. 1177–1187, Feb. 1, 1995.
Coffman et al. J Exp. Med. 170: 1039–1044 (1989).
Sonoda et al. J. Exp. Med. 170: 1415–1420 (1989).
Kunimoto et al. Eur Cytokine Netw 3(4): 407–415 (1992).
Heath et al. Vaccine 10: 427–434 (1992).
Pecanha et al. J. Immunol 146: 833–839 (1991).

*Primary Examiner*—Christina Y. Chan
*Assistant Examiner*—Phillip Gambel
*Attorney, Agent, or Firm*—Finnegan, Henderson, Farabow, Garrett & Dunner, L.L.P.

[57] ABSTRACT

The invention describes compositions and methods for optimizing IgA class switching in B cells. The compositions comprise a multivalent antigen receptor crosslinker, CD40 ligand or lipopolysaccharide, and the cytokines TGF-$\beta$, IL-4, and either IL-5 or IL-2. Methods of using the compositions are also described.

13 Claims, 5 Drawing Sheets

VACCINE FOR ENHANCED PRODUCTION OF IGA ANTIBODIES

This application is a continuation-in-part of application Ser. No. 08/315,492, filed Sep. 30, 1994, now abandoned, which is a continuation-in-part of application Ser. No. 08/150,510, filed Nov. 10, 1993, pending. Applicants specifically incorporate the prior applications by reference.

GOVERNMENT INTEREST

The invention described herein may be manufactured, licensed, and used for United States governmental purposes without the payment of any royalties to the inventors or assignee.

FIELD OF THE INVENTION

This invention relates to compositions and methods useful for optimizing antibody class switching to IgA antibodies by B lymphocytes. This increase is significant because IgA antibodies, as the major class of antibodies made in mucosal surfaces, are the primary class of antibodies responsible for protection against bacterial and viral infection.

BACKGROUND OF THE INVENTION

The human immune system comprises numerous different types of cells having overlapping functions which together act to protect the human body against sickness and disease. The cells of the immune system have complex multiple functions and interconnecting relationships. A major component of the immune system that plays an essential role in protecting the host against infection by these organisms is the humoral antibody.

Antibodies, also known as immunoglobulins, are protein molecules which have exquisite specificity for the foreign particle which stimulates their production. Immunoglobulins (Ig) are a class of structurally related proteins consisting of two pairs of polypeptide chains, one pair of light (L) [low molecular weight] chains ($\kappa$ or $\lambda$), and one pair of heavy (H) chains ($\gamma$, $\alpha$, $\mu$, $\delta$, and $\epsilon$), all four linked together by disulfide bonds. Both H and L chains have regions that contribute to the binding of antigen and that are highly variable from one Ig molecule to another. In addition, H and L chains contain regions that are nonvariable or constant.

The L chains consist of two domains. The carboxy-terminal domain is essentially identical among L chains of a given type and is referred to as the "constant" (C) region. The amino-terminal domain varies from L chain to L chain and contributes to the binding site of antibody. Because of its variability, it is referred to as the "variable" (V) region.

The H chains of Ig molecules are of several classes, $\alpha$, $\mu$, $\delta$, $\alpha$, and $\gamma$ (of which there are several subclasses). An assembled Ig molecule, consisting of one or more units of two identical H and L chains, derives its name from the H chain that it possesses. Thus, there are five Ig isotypes: IgA, IgM, IgD, IgE, and IgG (with four subclasses based on differences in the H chains, i.e., IgG1, IgG2, IgG3, and IgG4).

Not all antibody isotypes are equal in the performance of the many biological roles of antibodies. For example, IgA, primarily present in secretions such as tears, urine, saliva, colostrum, sweat, and mucus (i.e., secretory IgA) is the major immunoglobulin synthesized in the body. It is believed to be the primary immunological defense against local infections in such areas as the respiratory or gastrointestinal tract. Secretory IgA is also an efficient antiviral antibody, preventing the viruses from entering host cells, as well as an efficient agglutinating antibody.

The actions of the very versatile and long-lived IgG ranges from neutralization of toxin to activation of complement and opsonization. For example, IgG reacts with epitopes on microorganisms via its Fab portions leading to the final engulfing and destruction of the microorganism. It also plays an important role in antibody-dependent, cell-mediated cytotoxicity (ADCC) by activating natural killer cells which then destroy the target by release of various substances. It is also an effective virus neutralizing antibody.

In contrast to IgG, IgM antibodies are not very versatile; they are poor toxin-neutralizing antibodies, and they are not very efficient in the neutralization of viruses. IgM is found predominantly in the intravascular spaces and is the isotype synthesized by children and adults in appreciable amounts after immunization or exposure to T-independent antigens, and is the first isotype that is synthesized after immunization with T-dependent antigens. IgM molecules are the most efficient agglutinating and complement-activating antibodies.

IgD molecules, present on the surface of B lymphocytes, appear to be involved in the differentiation of these cells and generally have not been demonstrated to serve a protective function.

IgE, also called reaginic antibody, is of paramount importance in hypersensitivity or allergy reactions. These reactions may be mild, such as in the case of a mosquito bite, or severe, as in the case of bronchial asthma. The reactions may even result in systemic anaphylaxis, which can cause death within minutes.

Despite this variability, all immunoglobulins derive from antibody-secreting cells. The precursors of the antibody-secreting cell are B lymphocytes, also known as "B cells." B cells are a type of lymphocyte that derives from hematopoietic stem cells by a complex set of differentiation events that are only partially understood.

B cells bear as a cell-surface receptor an immunoglobulin (Ig) molecule specialized for expression on the cell surface. Newly differentiated B cells initially express surface Ig solely of the IgM class. Associated with maturation of a B cell is the appearance of other immunoglobulin isotypes on the surface of the B cell.

To release antibody, the B cells must first be activated. There are many ways to activate B cells, including cross-linkage of membrane (m) Ig molecules by the antigen mIg (cross-linkage-dependent B cell activation), direct encounter with T cells (helper T cells or helper T cell-associated molecules, such as, for example, CD40 ligand), or encounter with mitogens. In such encounters, the antigen presents epitopes recognized by the B cell's cell-surface Ig.

Because each B cell bears multiple membrane Ig molecules with identical variable regions, high level cross-linkage of the cell-surface receptors yields optimal activation. This cross-linkage requires that the antigen present more than one copy of the epitope that the cell-surface Ig recognizes. Although many simple protein antigens do not have this potential, polysaccharides and other antigens with repeating epitopes, such as surfaces of microbes and DNA, do. Among these more complex antigens are the capsular polysaccharides of many medically important microorganisms, such as pneumococci, streptococci, and meningococci.

There are much data to show that cross-linkage of membrane Ig can also lead to elimination or inactivation of B cells. In general, it is believed that certain types of receptor cross-linkage events, if they occur in the absence of specific stimulatory signals, lead to inactivation rather than activation. The highly repetitive epitopes expressed on polysaccharides may lead to activation in the absence of costimulation, possibly because of the magnitude of the receptor-mediated stimulation.

Once the B cells which initially express IgM and/or IgD on their surface, are activated the antibodies that are initially produced are primarily of the IgM isotype. Most interestingly, in response to a specific challenge, T cell help allows B cells to "class switch" their particular V region to an appropriate C region (i.e., to a region corresponding to γ, α, and ε). Thus, a cell that expresses receptors of the IgM and IgD classes may differentiate into a cell that expresses IgG, IgA, or IgE receptors and then into a cell that secretes those antibodies. This process allows the production of different antibodies with their distinct biological functions against the same antigen that first induced the antibody response.

The induction of the switching process depends upon the action of a specialized set of B cell stimulants. Studies have identified two different kinds of stimuli that are important for the induction of isotype switching. The first kind of stimuli are predominantly responsible for the specificity of the isotype-switch event. These include, but are not limited to, the cytokine IL-4, interferon-γ (IFN-γ), and transforming growth factor-β (TGF-β). They are all characterized by the ability to induce the transcription of an immature (germline) form of RNA for the heavy chain isotype to which switching will be induced. Stimuli that induce switching to one isotype often stimulate switching to an additional isotype and inhibit switching to other isotypes.

The second kind of stimuli, or combinations of stimuli, activates B cells and often results, by themselves, in B cell proliferation and Ig secretion without isotype switching. These stimuli may permit switching to occur to any of a number of different isotypes, depending on which of the specific stimuli are present, although some of the stimuli appear to block switching to some isotypes. These permissive stimuli include, but are not limited to, bacterial lipopolysaccharide (LPS), the cytokine IL-5, crosslinking of cell surface Ig, signals given by molecules on the cell membranes of activated T cells (for mouse B cells), infection with Epstein-Barr virus (EBV), crosslinking of CD40 ligand (a cell surface protein found generally on a specialized group of T cells), crosslinking of the tumor necrosis factor-α (TNF-α) receptor, and signals given by molecules on the cell membranes of activated T cells. Of these, the most widely studied are LPS (acting in the mouse but not in the human) and direct interaction of CD40 ligand.

Despite this information, the parameters necessary for induction of high-rate IgA class switching were unknown prior to this invention. Because IgA antibodies are an important line of defense against infection and disease, there is a need in the art for this knowledge. Such knowledge facilitates additional and superior methods of treating immune disorders.

SUMMARY OF THE INVENTION

The present invention fulfils a need in the art for new and improved immunotherapies. The novel compositions and methods enable improved and new treatments for immune disorders, as well as adjuvants for current immunotherapies.

This invention is directed to a composition and a method for the stimulation of optimal IgA antibody class switching by B cells comprising two B cell activators together with the cytokine known as TGF-β. Other cytokines may also be employed.

In a preferred embodiment, one of the B cell activators is a multivalent Ig-receptor crosslinker. The other B cell activator, which works through other receptors, is preferably either a CD40 ligand or LPS, depending on the host. In humans, only CD40 ligand is employed. Of the additional cytokines, a preferred cytokine is IL-4 in combination with either IL-5 or IL-2. Of course, molecularly engineered fragments of TGF-β, IL-4, IL-5, and IL-2 that retain the activity of the cytokine can also be employed in the invention.

Methods of stimulating and inhibiting the release of antibody by B cells can be used to bolster mammalian immune responses to, for example, vaccination under conditions of normal or immunocompromised conditions.

Another object of the invention is a pharmaceutical composition comprising the novel compositions and a pharmaceutically acceptable carrier.

A further object of this invention is the use of the novel methods and compositions as adjuvants for vaccines. For example, many vaccines are currently administered intravenously or intramuscularly to allow a rapid stimulation of immune cells present in the blood system. By combining the novel compositions, either as a fusion protein covalently linked to a carrier molecule, admixed, or any other combination, with a vaccine to be administered, the magnitude of the IgA antibody response can be increased, both at the systemic and local levels.

Other objects and advantages of the present invention will be set forth in part in the description which follows, and in part will be obvious from this description, or may be learned from the practice of this invention. The accompanying drawings and tables, which are incorporated in and constitute a part of this specification, illustrate and, together with this description, serve to explain the principle of the invention.

DESCRIPTION OF PREFERRED EMBODIMENTS

The invention describes compositions and methods for stimulating antibody class switching. As set forth above, antibody classes are determined by the H chains classes, α, μ, δ, ε, and γ (with four subclasses), which correspond to IgA, IgM, IgD, IgE, and IgG (with four subclasses). As is understood in this art, class switching is the process whereby B cells that initially express either IgM and/or IgD switch to the expression of IgE, IgA, or one of the four IgG subclasses. Those B cells then secrete the Ig that they express. Class switching can involve both increasing and decreasing expression and the corresponding secretion.

Previous in vitro studies defined parameters which generated up to only 1–2% membrane IgA$^+$ cells. By contrast, the primary site for IgA class switching in vivo, Peyer's patches, exhibit switching at a rate of 10–20% of the total B cell population but the mechanism for this is unknown. The present invention defines a set of in vitro parameters that induce IgA switching to 15–20% of the total B cell population. Such an increase is a non-limiting example of a stimulated class switching.

As used herein, a B cell is a type of lymphocyte, also known as the B lymphocyte, that is the precursor for antibody-secreting cells. It bears at least two types of cell surface receptors to which activators may attach to activate the B cell. As those in the art understand, a cell surface receptor is a macromolecule that has a known binding affinity for a specific ligand. One of the B cell surface receptors is an immunoglobulin molecule that is specialized for expression on the cell surface, here termed Ig-receptors for convenience. Other receptors include Fc receptors, complement receptors, and others, here termed non-Ig-receptors for convenience.

A primary example of a potent Ig-receptor activator is known as dextran conjugated monoclonal anti-IgD or αδ-dex which mediates multivalent Ig-receptor crosslinking. To prepare αδ-dex, Hδa/1 (monoclonal mouse IgG2b (b allotype)) and anti-mouse IgD (a allotype) are conjugated to a high m.w. dextran ($2\times10^6$ kd) as described in Mond et al., *J. Immunol.* 140:3364 (1988) and Mond et al., *J. Immunol.* 146:833 (1991), herein incorporated by reference. Anti-IgD antibodies may be conjugated to dextran at a ratio of 9:1. Of course, other multivalent Ig-receptor activators are within the scope of this invention.

Although those in the art would be familiar with the greater number of known non-Ig-receptor activators, two are particularly suitable for the claimed invention, i.e., CD40 ligand and bacterial lipopolysaccharide (LPS). Of course, when the host is human, LPS is not a suitable activator. Persons of ordinary skill in this art would also be well familiar with the sources for both these receptor activators as well as the appropriate amounts. CD40 ligand is preferably present at about 10 μg/ml and LPS at 20 μg/ml. The amount of this B cell receptor activator influences the preferable amount of the multivalent antigen receptor crosslinker. For example, the multivalent antigen receptor crosslinker is present at about 3 ng/ml for LPS costimulation in vitro and at about 0.3 ng/ml for CD40 ligand costimulation in vitro.

Such persons would also be familiar with methods to cross link these receptors. For example, a receptor could be inserted into membranes, such as insect cell membranes, to form a extensively cross-linked construct. A preferred construct is a CD40 ligand/insect cell membrane. Membrane bound CD40 ligand is prepared from sf9 insect cells infected with a recombinant CD40 ligand-containing recombinant baculovirus vector.

As used herein, a "cytokine" is a member of a class of compounds that regulate responses of cells of the immune system, such as B and T lymphocyte cells ("B cells" and "T cells") and natural killer ("NK") cells. "Cytokine" is a generic term for a nonantibody protein released by certain cell populations on contact with an inducer and which acts as an intercellular mediator. A "lymphokine" is a soluble substance released by sensitized lymphocytes on contact with specific antigen or other stimuli which helps effect cellular or humoral immunity. The terms "cytokine" and "lymphokine" have become interchangeable. In an attempt to simplify the nomenclature of these compounds, a group of participants at the Second International Lymphokine Workshop held in 1979 proposed the term "interleukin," abbreviated "IL," to develop a uniform system of nomenclature based on the ability of the proteins to act as communication signals between different populations of leukocytes.

To date, 21 different cytokines, most but not all of which are produced by T cells, have been identified. Each has a distinct molecular configuration and performs a different task. A number of the known cytokines have been shown to have a demonstrable activity on B cells. In vitro, IL-1, IL-2, IL-4, IL-5, IL-6, IL-10, IFN-γ, and TGF-β (transforming growth factor β) have been shown to enhance B cell proliferation, immunoglobulin secretion, and/or to otherwise play a role in influencing the subclass of secreted Ig. Depending on the system being studied, addition of either one or a number of the above lymphokines has been shown to increase in vivo antibody production or to alter the isotype (i.e., IgG, IgM, IgE, IgA, etc.) of secreted antibody. These cytokines typically have effects on both processes.

TGF-β is synthesized predominantly by T cells, monocytes, and platelets. This factor is known to inhibit the activation of T cells and monocytes, as well as enhancing the production of IgA. In culture, most cells of the immune system, such as lymphocytes and monocytes, synthesize TGF-β. Treatment of lymphocytes and monocytes with TGF-β results in a large array of biological responses, dependent on the cell type and its differentiation state. For example, TGF-β inhibits the proliferation of B lymphocytes, and in addition, suppresses the expression by activated B lymphocytes of membrane immunoglobulin and decreases secretion of immunoglobulin G and M. It is also known that the presence of TGF-β promotes murine B cells stimulated with lipopolysaccharide to undergo isotype switching to IgA, whereas the continued presence of TGF-β inhibits IgA secretion.

Other cytokines that play a role in host protection include IL-2, IL-4 and IL-5. IL-2, also known as T cell growth factor, is a polypeptide hormone produced by both T helper and suppressor lymphocytes. This cytokine stimulates the growth and differentiation of T cells, B cells, NK cells, lymphokine-activated killer (LAK) cells, monocytes, macrophages, and oligodendrocytes.

IL-4 is a glycoprotein also known as B cell stimulating factor 1 (BSF-1) and B cell differentiation factor. It functions to costimulate B cell growth, Ig class switching, T cell growth and differentiation, macrophage activation, regulate mast cell growth, and to costimulate hematopoietic precursor cells.

IL-5, also known as B cell growth factor II (BGF-II), T cell replacing factor, IgA-enhancing factor, and eosinophil colony stimulating factor, is a glycoprotein produced by T lymphocytes and mast cells. This cytokine has the dual functions of a colony stimulating factor, as well as promoting the differentiation of eosinophilic colonies in bone marrow. IL-5 induces specific in vitro antibody production by B cells primed with antigen in vivo. While IL-5 serves as a differentiation factor in vitro, it does not appear to act as a differentiation factor in vivo.

Although those in this art could determine the appropriate amounts of cytokine, preferable amounts of TGF-β are about 10 ng/ml, of IL-4 are about 1000 U/ml, and of IL-5 are about 150 U/ml in vitro for optimizing IgA antibody class switching. In vivo amounts are scaled up accordingly, as is well known in the art.

Having now described the basic components of the invention, we provide the following supporting information.

A. Identification of Parameters Necessary for High-rate IgA Class Switching

One major obstacle to understanding the mechanisms which underlie physiologic class switching to IgA has been the inability to establish an in vitro system for high-rate IgA class switching. TGF-β has been established as a switch factor for the murine IgA class on the basis of its ability to selectively stimulate germline α RNA (Coffman, et al., *J. Exp. Med.* 7:1039 (1989); Sonoda et al., *J. Exp. Med.* 170:1415 (1989)) and induce large increases in IgA secretion by LPS-activated cells, especially when acting in concert with IL-2 or IL-5. (Coffman, et al., *J. Exp. Med.* 170:1415 (1989)). However, IgA secretion under these conditions was associated with the generation of only a few percent membrane (m)IgA$^+$ cells. This implied a requirement for additional stimuli to account for the substantially higher (i.e. 10–20%) percentages of mIgA$^+$ cells found in the Peyer's patch (Butcher, E., C., R. V. Rouse, R. L. Coffman, C. N. Nottenburg, R. R. Hardy, and I. L. Weissman, 1982, Surface phenotype of Peyer's patch germinal center cells; implications for the role of germinal centers in B cell differentiation. *J. Immunol.* 129;2698), the primary site for IgA class switching in vivo.

1. Multivalent antigen receptor cross-linking of CD40L- or LPS-activated B cells, plus IL-4, IL -5, and TGF-β induces a large percentage of mIgA+ cells To establish an in vitro system for high-rate IgA class switching, TGF-β was tested with various combinations of B cell activators with a number of cytokines known to be active in regulating the class switch.

Figure 1:
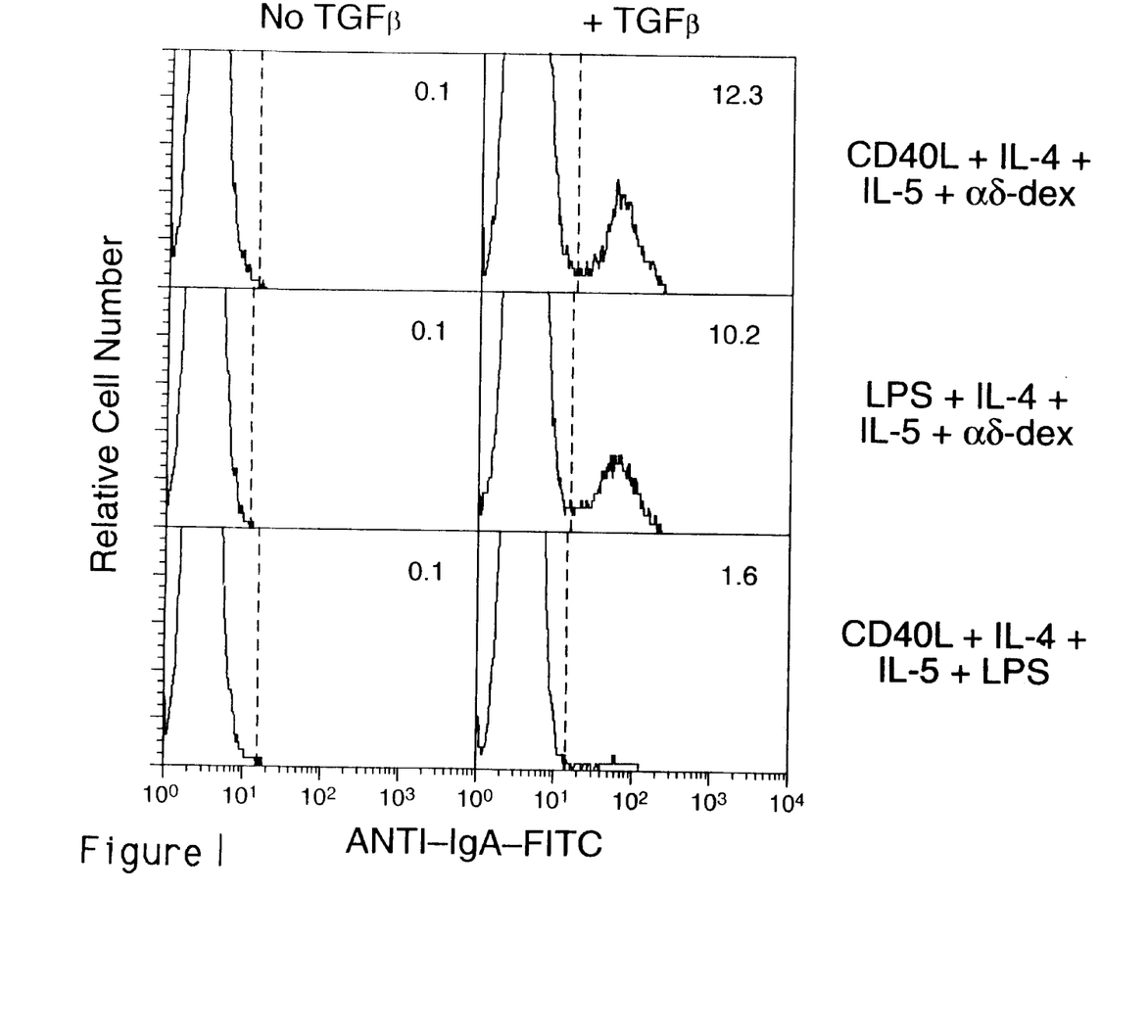
FIG. 1: flow cytometric analysis of membrane (m)IgA+ cells to assess IgA class switching in response to activation with dual combinations of a multivalent cross-linked antigen (dextran-conjugated anti-Ig antibody, or αδ-dex), CD40L, and/or LPS, plus IL-4+IL-5, in the presence or absence of TGF-β.

Flow cytometric analysis of mIgA+ cells was performed to assess IgA class switching in response to activation with dual combinations of the multivalent cross-linked antigen receptor, as mediated by dextran-conjugated anti-Ig antibody in the experimental model (αδ-dex), CD40L, and/or LPS, plus IL-4+IL-5, in the presence or absence of TGF-β (FIG. 1). In the absence of TGF-β, no significant induction of mIgA$^+$ cells was seen, regardless of the method of activation. In the presence of TGF-β, IL-4+IL-5, and activation with αδ-dex and either LPS or CD40L, 10% and 12% mIgA$^+$ cells, respectively were generated. This is greater than a 100-fold increase in the percentage of mIgA$^+$ cells over that seen in the absence of TGF-β.

In contrast to costimulation in the presence of a multivalent antigen receptor crosslinker (αδ-dex), dual activation with CD40L+LPS resulted in comparatively low levels of mIgA$^+$ cells.

TGF-β was selective for induction of mIgA$^+$ cells following costimulation with LPS, a multivalent antigen receptor crosslinker (αδ-dex), IL-4, and IL-5 in that TGF-β did not induce mIgG2b$^+$ or mIgG3$^+$ cells nor did it affect the percentage of mIgG1$^+$ cells induced in the presence of IL-4.

2. Optimal induction of IgA class switching by either LPS- or CD40L-activated cells requires the independent actions of a multivalent antigen receptor crosslinker, IL-4, IL-5, and TGF-β

Figure 2:
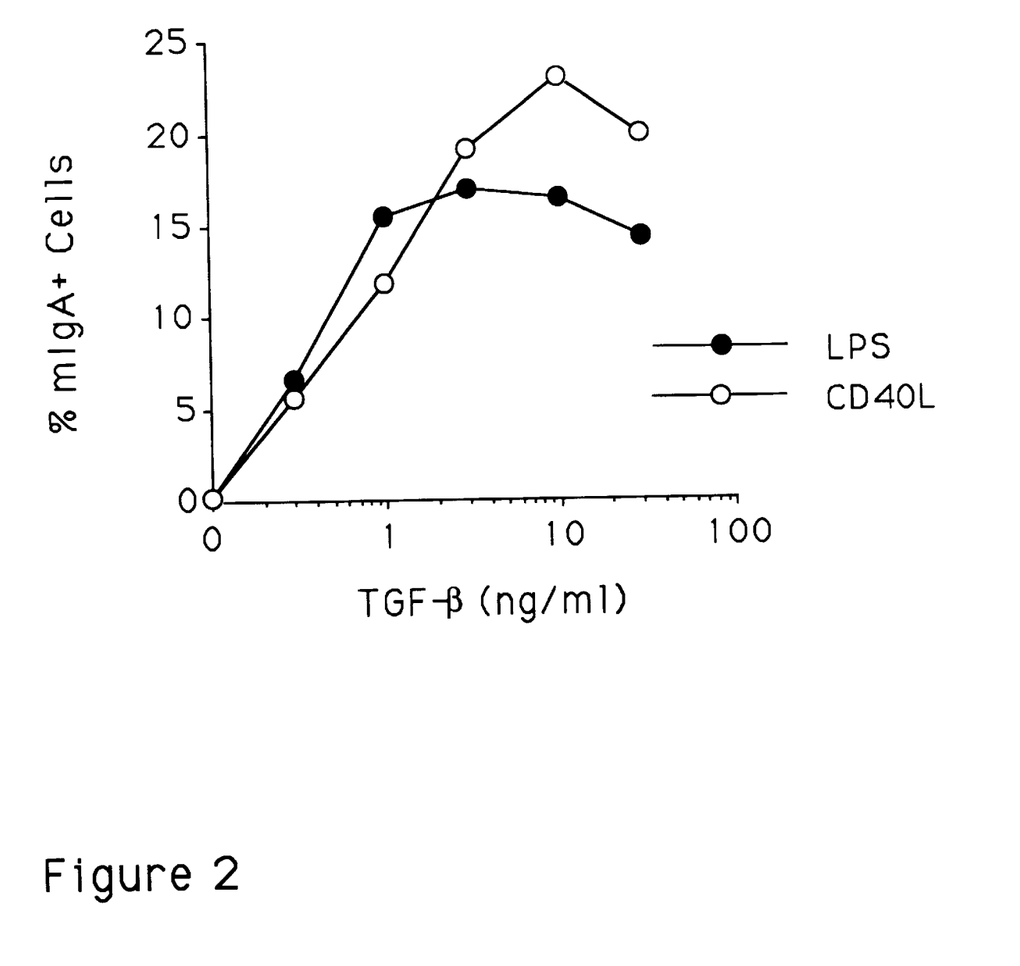
FIG. 2: the percentages of mIgA$^+$ cells generated in response to LPS or CD40L, in the presence or absence of TGF-β, with or without αδ-dex, IL-4, and/or IL-5, was measured to determine the relative requirements of the various stimuli for generating optimal IgA class switching.

To determine the relative requirements of the various stimuli for generating optimal IgA class switching, the percentages of mIgA$^+$ cells generated in response to stimulation by LPS or CD40L, in the presence or absence of TGF-β, with or without a multivalent antigen receptor crosslinker (αδ-dex), IL-4, and/or IL-5 were measured (FIG. 2).

TGF-β stimulated a modest increase in mIgA$^+$ cells in cultures activated with most combinations of stimuli, but these percentages did not exceed 2%. Only in the combined presence of a multivalent cross-linked antigen receptor (αδ-dex), IL-4, IL-5, and TGF-β were relatively large percentages of mIgA$^+$ cells generated upon activation with either LPS or CD40L (11.0% and 12.3%, respectively).

3. TGF-β induction of mIgA+ cells is associated with selective stimulation of IgA secretion Costimulation of B cells with either LPS+ a multivalent antigen receptor crosslinker (αδ-dex), or CD40L+αδ-dex, in the presence of IL-4, IL-5, and TGF-β, stimulated a greater than 34 fold, and a greater than 176-fold induction in IgA secretion, respectively, compared to that obtained in the absence of TGF-β (Table 1).

This enhancement in IgA secretion was selective in that the concentrations of most other Ig isotypes were significantly suppressed. The modest induction of IgG3 and IgG2b secretion in this system was not substantially affected by the presence of TGF-β.

4. A multivalent antigen receptor crosslinker strongly augments proliferation of LPS- or CD40L-activated cells and allows for vigorous cell growth in the presence of high concentrations of TGF-β

The induction of class switch recombination may require active DNA synthesis (Dunnick, W., and J. Stavnezer. 1990. Copy choice mechanism of immunoglobulin heavy-chain switch recombination. *Mol. Cell. Biol.* 10:397). Hence, although TGF-β may target the $C_H\alpha$ gene for recombination, as evidenced by its induction of $C_H\alpha$ germline RNA, its anti-proliferative effects may dampen the subsequent level of $C_H\alpha$ gene rearrangement.

To determine the contribution made by the individual components in the system described on the level of DNA synthesis, $^3$H-TdR incorporation in response to various combinations of stimuli was measured.

Figure 3:
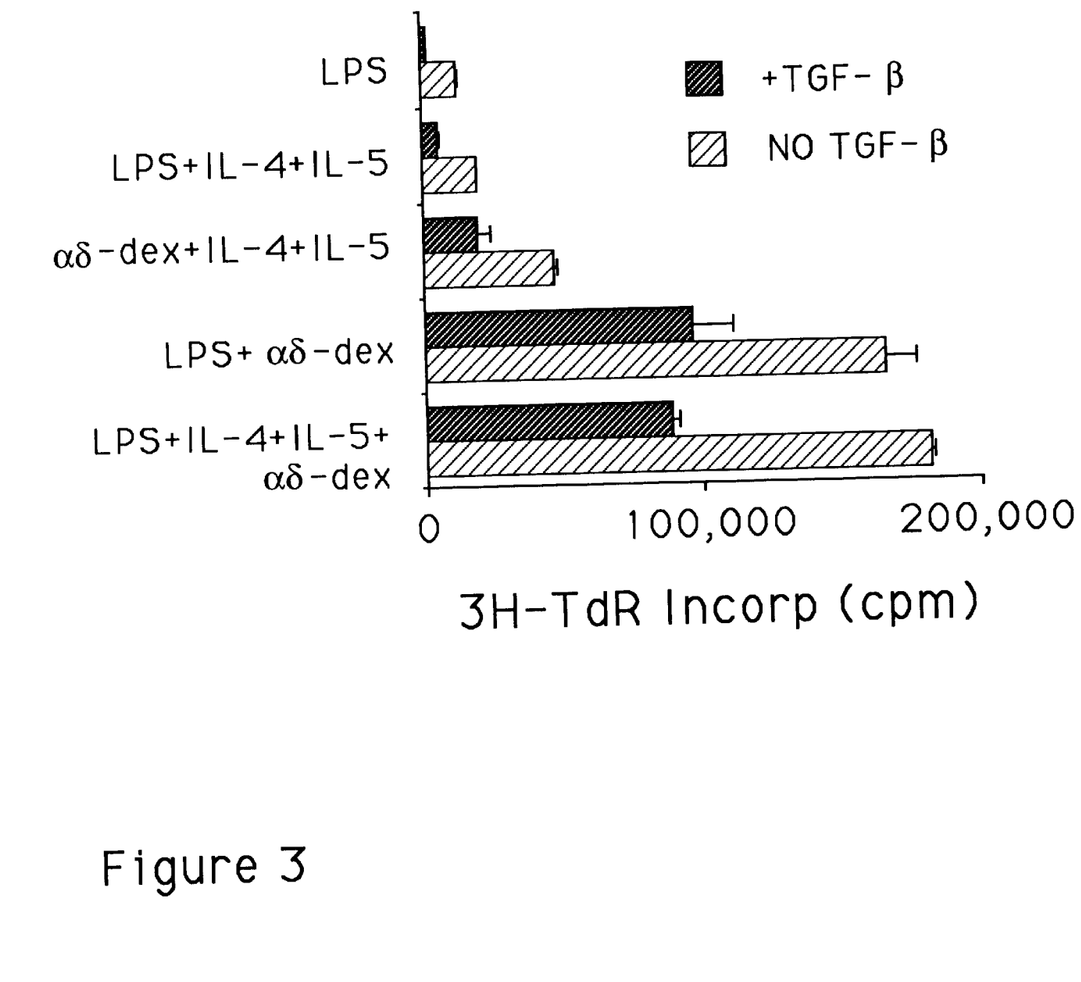
FIG. 3: the $^3$H-Tdr incorporation in response to various combinations of stimuli was measured to determine the contribution made by the individual components in the system on the level of DNA synthesis.

In the absence of TGF-β, the multivalent antigen receptor crosslinker (αδ-dex) strongly enhanced $^3$H-Tdr incorporation by LPS-activated cells (FIG. 3). The combination of IL-4+IL-5 had little effect on proliferation in response to either LPS or LPS+αδ-dex. In the presence of high concentrations of TGF-β, although DNA synthesis was variably inhibited under all conditions, compared to that seen in the absence of TGF-β, only in the presence of both activators LPS+αδ-dex, in the presence or absence of IL-4+IL-5, was relatively high levels of DNA synthesis maintained. Similar results were obtained when CD40L was used instead of LPS. The combination of CD40L and LPS also allowed for relatively high levels of growth in the presence of TGF-β, independent of IL-4+IL-5 but did not result in increased percentages of mIgA$^+$ cells (see FIG. 1). Therefore, enhanced proliferation is only a partial explanation for the role of a multivalent antigen receptor crosslinker in this system.

5. IL-2 can substitute for IL-5

Figure 4:
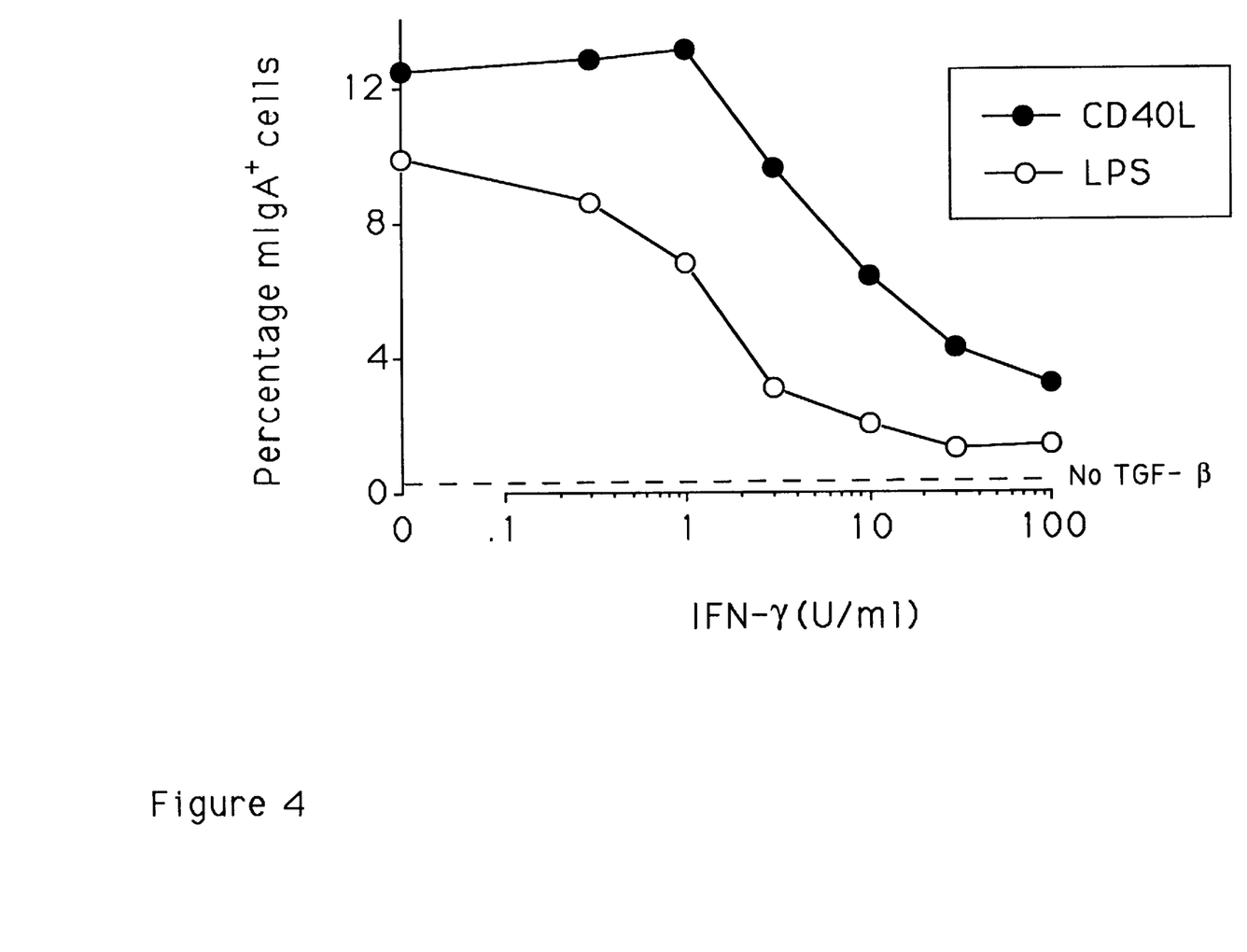
FIG. 4: IFN-γ was tested for suppression of the generation of mIgA$^+$ cells in the system to determine if it suppresses IgA class switching. IFN-γ strongly inhibited the percentage of mIgA$^+$ cells generated in response to activation with either LPS or CD40L in the presence of αδ-dex, IL-4, IL-5 and TGF-β.

IL-2 can substitute for IL-5 in stimulating IgA class switching by B cells activated by LPS/αδ-dex but not CD40L/αδ-dex. Resting DBA/2 splenic B cells were costimulated with LPS/αδ-dex or CD40L/αδ-dex in the presence or absence of the IL-4 and/or IL-5, TGF-β, and IL-2 (150 U/ml). LPS, CD40L, αδ-dex, IL-4, IL-5, and TGF-β, were used at dosages described in FIG. 1. Cells were harvested 5 days after initiation of culture for quantitation of mIgA+ B cells by flow cytometric analysis. 15,000 cells from each group were analyzed. The data of FIG. 4 is representative of two similar experiments.

6. IFN-γ suppresses IgA class switching

Figure 5:
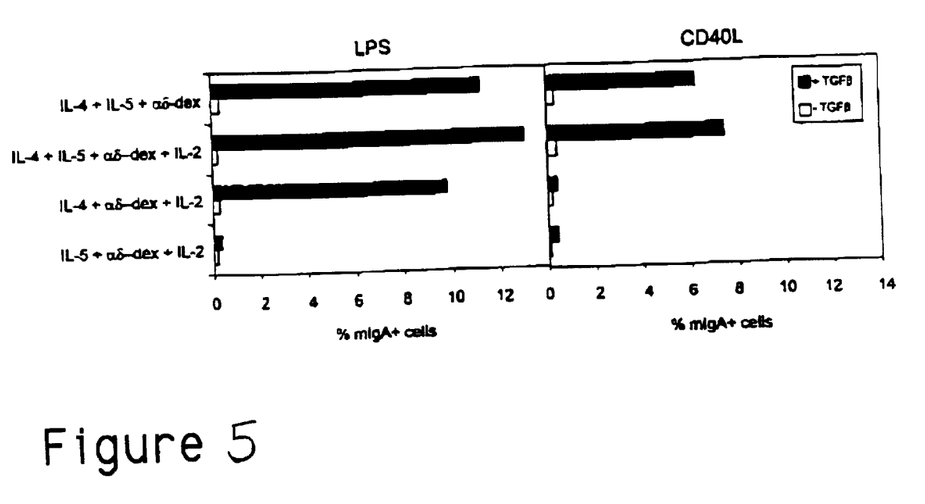
FIG. 5: IL-2 can substitute for IL-5 in stimulating IgA class switching by B cells activiated by LPS/αδ-dex but not CD40L/αδ-dex.

Since IFN-γ inhibits most IL-4-mediated effects on murine B cells, and since IL-4 was a key component for inducing IgA class switching, IFN-γ was tested to determine if it could suppress the generation of mIgA$^+$ cells in this system (FIG. 5).

IFN-γ strongly inhibited the percentage of mIgA$^+$ cells generated in response to activation with either LPS or CD40L in the presence of a multivalent cross-linked antigen receptor (αδ-dex), IL-4, IL-5, and TGF-β. Optimal inhibition of IgA class switching occurred at 100 U/ml of IFN-γ representing an ~4-fold and ~6-fold suppression for CD40L- and LPS-activated cells, respectively. A significant reduction in mIgA$^+$ cells was observed with as little as 1–3 U/ml of IFN-γ.

7. The activity of CD40 ligand

Published data suggests that the activity of CD40 ligand may depend on the absolute amount of this protein expressed on the cell surface. In view of this, we compared the ability of soluble CD40 ligand (sCD40L) and membrane CD40L (mCD40L) which expressed a higher density of CD40L than sCD40L, to stimulate Ig secretion. Sort purified B cells were altered as in earlier experiments [cells were cultured in flat bottom 96 well plates at $2 \times 10^5$/ml with complete medium. Concentrations of CD40L were as indicated, and anti-Ig-dextran at 0.3 ng/ml; supernatants were collected at day 6 and Ig concentration determined by ELISA] with anti-Ig-dextran and sCD40L or mCD40L. While the latter was far more stimulatory for IgM and IgG1 secretion, it was markedly inhibitory for secretion of IgE as compared to sCD40L which was markedly stimulatory. This supports the use of mCD40L or agonists similar to it, which are extremely stimulatory for beneficial Ig isotypes but inhibitory for IgE which may promote allergic responses.

The mechanisms underlying the requirement for the combined actions of the cytokines IL-4, IL-5, and TGF-β along with the B cell activators of a multivalent antigen receptor crosslinker, and LPS or CD40L, for inducing relatively high-rate IgA class switching are unknown.

Regardless of the mechanism, these data suggest a rather stringent, complex requirement for inducing high percentages of mIgA$^+$ cells under physiologic conditions. The fact that splenic B cells, as used in these studies, can undergo vigorous IgA class switching suggests that the pattern of stimulation, and not the intrinsic nature of the resident B cells, accounts for this phenomenon. Although any of the IgA-inductive stimuli identified here become manifest in any immunologic site, the sequestration of IgA class switching within the Peyer's patch could, in part, reflect the constitutive and simultaneous action of high levels of multiple stimuli on the resident B cells, as a result of their unique proximity to and communication with the complex microbial and antigenic milieu of the gastrointestinal tract. Thus, the concomitant exposure to multiple proteins with consequent recruitment of T cell help, as well as T-independent antigens including mitogens, and polysaccharides which could deliver multivalent antigen-receptor-mediated signals, could allow for vigorous IgA class switching to occur in response to TGF-β.

B. Use of the Claimed Compositions

Parent application Ser. No. 08/315,293, filed Sep. 30, 1994, teaches composition and methods for stimulating the release of antibody by B cells. The compositions and methods of the parent application can be combined with the present invention for new and improved immunotherapies.

1. Treatments based on the composition

Treatment comprises administering the pharmaceutical composition by intravenous, intraperitoneal, intracorporeal injection, intra-articular, intraventricular, intrathecal, intramuscular, subcutaneous, intranasally, intravaginally, orally, or by any other suitable method of administration. The composition may also be given locally, such as by injection to the particular area, either intramuscularly or subcutaneously.

Suitable hosts for treatment include any suitable mammal. Preferred hosts are humans, including neonates, adults, and immunodeficient patients.

The dosage of the compounds employed varies depending upon age, individual differences, symptoms, mode of administration, etc., and can be readily determined by one of skill in the art. Exemplary dosages of the cytokines TGF-β, IL-4, IL-5, and IL-2 are given in McIntyre, T. M., Kehry, and Snapper, C. M., 1995, A novel in vitro model for high-rate IgA class switching, *J. Immunol.* (In press). Exemplary dosages of CD40 ligand are given in McIntyre, T. M., Kehry, and Snapper, C. M., 1995, A novel in vitro model for high-rate IgA class switching, *J. Immunol.*, and exemplary dosages of a multivalent antigen receptor crosslinker are given in McIntyre, T. M., Kehry, and Snapper, C. M., 1995, A novel in vitro model for high-rate IgA class switching, *J. Immunol.*

Any pharmaceutically acceptable carrier can be employed for the multivalent antigen receptor crosslinker, CD40 ligand, TGF-β, IL-4, and either IL-5 or IL-2. Carriers can be sterile liquids, such as water, oils, including petroleum oil, animal oil, vegetable oil, peanut oil, soybean oil, mineral oil, sesame oil, and the like. With intravenous administration, water is a preferred carrier. Saline solutions, aqueous dextrose, and glycerol solutions can also be employed as liquid carriers, particularly for injectable solutions. Suitable pharmaceutical carriers are described in *Remington's Pharmaceutical Sciences*, 18th Edition (A. Gennaro, ed., Mack Pub., Easton, Pa., 1990), incorporated by reference.

2. Vaccine adjuvants comprising the compositions

This invention also encompasses vaccine adjuvants comprising the compositions of the invention. Many vaccines are currently administered intravenously or intramuscularly to allow a rapid stimulation of immune cells present in the blood system. By combining the novel compositions with a drug to be administered, the magnitude of the IgA antibody response is increased, both locally and systemically.

In the in vitro assay, the anti-IgM or anti-IgD antibody when presented in a multivalent form, such as dextran, acts efficiently to activate all B cells. Thus, the in vitro model employing anti-Ig-dextran acts to cross-link all antigen receptors. However, this response is not desired in vivo. In a patient, the goal is to activate only a small number of B cells having receptors specific for the antigen. The specific antigen of the vaccine acts to cross-link specific B cell receptors. Thus, the multivalent antigen receptor crosslinker would employ the antigen of the vaccine.

Preferably, when used as a vaccine adjuvant, the compositions of the invention are conjugated to a multivalent carrier molecule, such as dextran or a capsular polysaccharide of a bacteria. Pneumococci, streptococci, and meningococci capsular polysaccharides are preferred. In addition, CD40 ligand and the cytokines TGF-β, IL-4, and either IL-5 or IL-2, molecularly engineered fragments of these cytokines that retain the activity of the cytokines, can be independently or in any combination conjugated to the multivalent carrier. The cytokines can also be fused together or fused to another protein to form a fusion protein, which can also be bound to the multivalent carrier. The multivalent cross-linked antigen receptor can also serve as the carrier molecule for CD40 ligand and TGF-β, IL-4, and either IL-5 or IL-2. Other vaccine variations will be apparent to one of skill in the art.

This application encompasses the use of anti-cytokine—cytokine complexes which allow for the slow but prolonged delivery of the cytokine. The complexes can be administered as a mixture with the antigen of a vaccine, or the complexes can be bound to the antigen of a vaccine.

In still another embodiment, the vaccine adjuvant can comprise CD40 ligand, one or more cytokines other than GM-CSF, IL-3, or IFN-γ, or a combination thereof. CD40L and the one or more cytokines can also be bound to the multivalent carrier.

3. Compositions used in a conjugate vaccine

To form a conjugate vaccine, the antigen of the vaccine and the compositions of the invention can be covalently conjugated to a multivalent carrier molecule, such as dextran or a capsular polysaccharide of a bacteria. Pneumococci, streptococci, and meningococci capsular polysaccharides are preferred.

The antigen is a peptide or protein specific for the disease to be vaccinated against.

To further optimize the humoral immune response upon administration of the vaccine, CD40 or at least one other cytokine, or a combination thereof, can be conjugated to the multivalent carrier.

Table II shows exemplary compositions of the invention. As noted in the Table, several of the vaccines are conjugate vaccines. Methods of conjugation are well known to those of ordinary skill in the art, and include the heteroligation techniques of Brunswick et al., *J. Immunol.*, 140:3364 (1988); Wong, S. S., *Chemistry of Protein Conjugates and Crosslinking*, CRC Press, Boston (1991); and Brenkeley et al., "Brief Survey of Methods for Preparing Protein Conjugates With Dyes, Haptens and Cross-Linking Agents," *Bioconjugate Chemistry*, 3, No. 1 (January 1992), specifically incorporated by reference.

The unexpected effect of the present invention is demonstrated in the following experiments and is depicted in FIGS. 1–4.

Having generally described the invention, a more complete understanding can be obtained by reference to specific examples, which are provided herein for purposes of illustration only and are not intended to be limiting.

EXAMPLE 1

This example shows that multivalent antigen receptor cross-linking of CD40L- or LPS-activated B cells, plus IL-4, IL-5, and TGF-β induces a large percentage of mIgA+ cells.
Materials and Methods:

Mice: Female DBA/2 mice were obtained from the National Cancer Institute (Frederick, Md.) and were used at 8–12 weeks of age.

Culture medium: RPMI 1640 (Biofluids, Rockville, Md.) supplemented with 10% FCS (Sigma Chemical Co., St. Louis, Mo.), L-gluamine (2 mM), 2-mercaptoethanol (0.05 mM), penicillin (50 μg/ml), and streptomycin (50 μg/ml) was used for culturing cells.

Reagents: Dextran conjugated monoclonal anti-IgD (Hδa/1) (αδ-dex) was prepared by conjugation of Hδa/1 (monoclonal mouse IgG2b (b allotype)), anti-mouse IgD (a allotype) to a high m.w. dextran ($2 \times 10^6$ kd). Anti-IgD antibodies were conjugated to dextran at a ratio of 9:1.

Recombinant CD8–CD40 ligand (L) fusion protein was constructed and expressed as described in Lane, P., T. Brocker, S. Hubele, E. Padovan, A. Lanzavecchia, and F. McConnell, 1993, Soluble CD40 ligand can replace the normal T cell-derived CD40 ligand signal to B cells in T cell-dependent activation, *J. Exp. Med.* 177:1209 and purified from culture supernatants by precipitation with ammonium sulfate and chromatography over a CM-Sepharose column. Endotoxin levels in purified CD8–CD40L were <0.02 ng/ml.

LPS W, extracted from *Escherichia coli* 0111:B4, was obtained from Difco Laboratories, Inc. (Detroit, Mich.). It was used at 20 μg/ml in all experiments.

Recombinant human TGF-β2 and purified, natural bovine TGF-β1 were kind gifts from Wendy Waegell (Celtrix Pharmaceuticals, Santa Clara, Calif.).

Murine rIL-5, prepared in the baculovirus system, was a kind gift from Dr. Richard Hodes (National Institutes of Health, Bethesda, Md.).

Murine rIL-4 (12 pg/U), produced in *E. coli*, was a generous gift from Dr. A. D. Levine (Monsanto Corporate Research, St. Louis, Mo.).

The following FITC-labelled, monoclonal antibodies were used as staining reagents for flow cytometric analysis: rat IgG1 anti-mouse IgA, rat IgG2a anti-mouse IgG2b, rat IgG2a anti-mouse IgG3, (Pharmingen, San Diego, Calif.), and rat IgG1 anti-mouse IgG1 (Zymed Laboratories, South San Francisco, Calif.). Monoclonal rat IgG2b anti-mouse FcγRII (2.4G2) (cite) was purified from ascites.

Preparation and culture of B cells: Enriched populations of small, resting T-depleted B cells were obtained from spleen as described in Snapper, C. M., and W. E. Paul, 1987, B cell stimulatory factor-1 (interleukin 4) prepares resting murine B cells to secrete IgG1 upon subsequent stimulation with bacterial lipopolysaccharide, *J. Immunol.* 139:10. Functional assays were carried out in 96- and 24-well flat bottomed Costar plates (Costar, Cambridge, Mass.). Cells were cultured at a final concentration of $1.25 \times 10^5$ cells/ml and incubated at 37° C. in a humidified atmosphere containing 6% $CO_2$.

Quantitation of secreted Ig isotypes: Ig isotype concentrations were measured by ELISA as described in Snapper, C. M., and W. E. Paul, 1987, B cell stimulatory factor-1 (interleukin 4) prepares resting murine B cells to secrete IgG1 upon subsequent stimulation with bacterial lipopolysaccharide. *J. Immunol.* 139:10.

Flow cytometric analysis of membrane (m)IgA+ cells was performed to assess IgA class switching in response to activation with the multivalent antigen receptor crosslinker, αδ-dex and CD40 ligand, αδ-dex and LPS, or CD40 ligand and LPS in the presence or absence of TGF-β (FIG. 1). IL-4 and IL-5 were also added to all of the test compositions.

The flow cytometric analysis was performed as described in Snapper, C. M., F. D. Finkelman, D. Stefany, D. H. Conrad, and W. E. Paul, 1988, IL-4 induces co-expression of intrinsic membrane IgG1 and IgE by murine B cells stimulated with lipopolysaccharide. *J. Immunol.* 141:489. Briefly, cells were first incubated for 20 min with 5 μg/ml final concentration of rat IgG2b anti-FcγRII mAb (2.4G2) to prevent cytophilic binding of FITC-labelled monoclonal antibodies, which were subsequently added at 10 μg/ml final concentration for an additional 30 min. All steps were carried out at 40C. Fluorescence analysis was accomplished on a FACScan (Becton Dickinson, Mountain View, Calif.) using logarithmic amplification. only viable cells, identified on the basis of their characteristic forward and side scatter profiles and their exclusion of propidium iodide (Sigma), were analyzed.

In the absence of TGF-β, no significant induction of mIgA⁺ cells was seen, regardless of the method of activation employed. In the presence of TGF-β, IL-4, and IL-5, and when B cells were activated with the multivalent antigen crosslinker αδ-dex and either LPS or CD40L, 10% and 12% mIgA⁺ cells were generated, respectively. This represents greater than a 100-fold increase in the percentage of mIgA⁺ cells over that observed in the absence of TGF-β. In contrast to costimulation in the presence of αδ-dex, dual activation with CD40L+LPS resulted in comparatively low levels of mIgA⁺ cells.

EXAMPLE 2

This example shows that optimal induction of IgA class switching by either LPS- or CD40L-activated B cells requires the independent actions of a multivalent antigen crosslinker, IL-4, IL-5, and TGF-β.

Materials and methods were as described in Example 1.

The percentage of membrane IgA cells secreted was measured for LPS- and CD40 ligand activated B cells treated with various combinations of cytokines and the multivalent antigen crosslinker αδ-dex: IL-4; IL-5; IL-4+IL-5; αδ-dex; αδ-dex+IL-4; αδ-dex+IL-5; and αδ-dex+IL-4+IL-5 (FIG. 2A for LPS-activated and FIG. 2B for CD40 ligand-activated B cells).

TGF-β stimulated a modest increase in mIgA⁺ cells in cultures activated with most combinations of stimuli, but these percentages did not exceed 2%. only in the combined presence of the multivalent antigen crosslinker αδ-dex, IL-4, IL-5, and TGF-β were relatively large percentages of mIgA⁺ cells generated upon activation with either LPS or CD40L (11.0% and 12.3%, respectively) (FIG. 1).

EXAMPLE 3

This example shows that TGF-β induction of membrane IgA cells (mIg+) is associated with selective stimulation of IgA secretion.

Materials and methods were as described in Example 1.

B cells were costimulated with either LPS+αδ-dex or CD40L+αδ-dex, in the presence of IL-4, IL-5, and TGF-β. Antibody isotype secretion in ng/ml was measured for IgM, IgG3, IgG1, IgG2b, IgG2a, IgE, and IgA. For the LPS-stimulated B cells, IgA was secreted at less than 25 ng/ml in the absence of TGF-β, and at 852 ng/ml in the presence of TGF-β, a 34 fold increase in secretion of IgA. Even more dramatic were the results observed with the CD40 ligand-activated B cells. In the absence of TGF-β IgA was secreted at less than 25 ng/ml. However, with the addition of TGF-β, IgA was secreted at 4,4000 ng/ml, a 176 fold increase in IgA secretion (Table 1).

This enhancement in IgA secretion was selective in that the concentrations of most other Ig isotypes were significantly suppressed. The modest induction of IgG3 and IgG2b secretion in this system was not substantially affected by the presence of TGF-β.

TABLE 1

| | Ig isotype secretion (ng/ml) | | | |
|---|---|---|---|---|
| | LPS + αδ - dex + IL-4 + IL-5 | | CD40L - αδ - dex + IL-4 + IL-5 | |
| Ig Isotype | No TGF-β | +TGF-β | No TGF-β | +TGF-β |
| IgM | 33,500 | 3,250 | 62,000 | 17,300 |
| IgG3 | 87 | <25 | 170 | 85 |
| IgG1 | 3,160 | 590 | 14,000 | 2,120 |
| IgG2b | 25 | 28 | <25 | 124 |
| IgG2a | <50 | <50 | <50 | <50 |
| IgE | 264 | <6 | 288 | 13 |
| IgA | <25 | 852 | <25 | 4,400 |

EXAMPLE 4

This example demonstrates that a multivalent antigen crosslinker strongly augments proliferation of LPS- or CD40L-activated cells and allows for vigorous cell growth in the presence of high concentrations of TGF-β.

Materials and methods were as described in Example 1.

The induction of class switch recombination may require active DNA synthesis (Dunnick, W., and J. Stavnezer, 1990, Copy choice mechanism of immunoglobulin heavy-chain switch recombination, Mol. Cell. Biol. 10:397. Hence, although TGF-β may target the $C_H\alpha$ gene for recombination, as evidenced by its induction of $C_H\alpha$ germline RNA (Lebman, D. A., D. Y. Nomura, R. L. Coffman, and F. D. Lee, 1990, Molecular characterization of germline immunoglobulin A transcripts produced during transforming growth factor type β-induced isotype switching, Proc. Natl. Acad. Sci. USA. 87:3962), its anti-proliferative effects (Kehrl, J. H., A. B. Roberts, L. M. Wakefield, S. Jakowlew, M. B. Sporn, and A. S Fauci, 1986, Transforming growth factor β is an important immunomodulatory protein for human B lymphocytes, J. Immunol. 137:3855), may dampen the subsequent level of CHα gene rearrangement. To determine the contribution made by the individual components in the system described on the level of DNA synthesis, ³H-Tdr incorporation was measured in response to various combinations of stimuli in the presence or absence of TGF-β: LPS; LPS+IL-4+IL-5; αδ-dex+IL-4+IL-5; LPS+αδ-dex; and LPS+αδ-dex+IL-4+IL-5 (FIG. 3).

DNA synthesis was determined by [³H]TdR uptake (2 μCi/well; 6.7 Ci/nmol; 1 mCi=37 GBq; ICN, Irvine, Calif.) over a 4 hr period. Cells were harvested (PHD cell harvester, Cambridge Technology, Watertown, Mass.) onto glass fiber filters and [³H]TdR incorporation was determined by liquid scintillation spectrometry.

In the absence of TGF-β, the multivalent antigen crosslinker αδ-dex strongly enhanced ³H-Tdr incorporation by LPS-activated cells (FIG. 3). The combination of IL-4+IL-5 had little effect on proliferation in response to either LPS or LPS+αδ-dex. In the presence of high concentrations of TGF-β, only in the presence of both LPS+αδ-dex, and in the presence or absence of IL-4+IL-5, was relatively high levels of DNA synthesis maintained. Similar results were obtained when CD40 ligand was used instead of LPS as a B cell activator. The combination of CD40L and LPS also allowed for relatively high levels of growth in the presence of TGF-β, independent of IL-4+IL-5 but did not result in increased percentages of mIgA⁺ cells (see FIG. 1). Therefore, enhanced proliferation is only a partial explanation for the role of a multivalent antigen crosslinker, such as αδ-dex, in this system.

The requirement for a multivalent antigen crosslinker for high-rate induction of IgA class switching in this system strongly suggested that the precursors of mIgA$^+$ cells in these cultures were mIgD$^+$ at initiation of culture and hence had not already switched to IgA. Further, since flow cytometric studies showed that costimulation with either CD40 ligand or LPS with αδ-dex in the presence of IL-4, IL-5, and TGF-β, resulted in greater than 100-fold increases in mIgA+ cells relative to cultures not receiving TGF-β, and since the overall expansion of cells by day 4 of culture was at best only 5-fold (data not shown), it is unlikely that the percentages of mIgA$^+$ cells generated in this system could be accounted for solely on the basis of a selective expansion of mIgA$^+$ cells.

EXAMPLE 5

This example demonstrates that IFN-γ suppresses IgA class switching.

Materials and methods were as described in Example 1. In addition, murine rIFN-γ (77 pg/U) prepared from Chinese hamster ovary cells, was a kind gift of Genentech (South San Francisco, Calif.).

IFN-γ inhibits most IL-4-mediated effects on murine B cells, and IL-4 is a key component for inducing IgA class switching. It was therefore determined whether IFN-γ could suppress the generation of mIgA$^+$ cells in the IgA switching system (FIG. 4).

IFN-γ strongly inhibited the percentage of mIgA$^+$ cells generated in response to activation with either LPS or CD40 ligand in the presence of αδ-dex, IL-4, IL-5 and TGF-β. Optimal inhibition of IgA class switching occurred at 100 U/ml of IFN-γ representing an ~4-fold and ~6-fold suppression for CD40 ligand- and LPS-activated B cells, respectively. A significant reduction in mIgA$^+$ cells was observed with as little as 1–3 U/ml of IFN-γ.

EXAMPLE 6

This example provides exemplary vaccines and vaccine adjuvants employing the compositions of the invention.

Table II shows exemplary vaccines employing the compositions of the invention. As noted in the Table, several of the vaccines are conjugate vaccines. Methods of conjugation are well known to those of ordinary skill in the art, and include the heteroligation techniques of Brunswick et al., *J. Immunol.*, 140:3364 (1988); Wong, S. S., *Chemistry of Protein Conjugates and Crosslinking*, CRC Press, Boston (1991); and Brenkeley et al., "Brief Survey of Methods for Preparing Protein Conjugates With Dyes, Haptens and Cross-Linking Agents," *Bioconjugate Chemistry*, 3, No. 1 (January 1992), specifically incorporated by reference.

The multivalent carrier replaces the multivalent conjugate (i.e., anti-IgD-dex) employed in vitro. Such a carrier can be, for example, a polysaccharide such as dextran, or a capsular polysaccharide from a bacteria, such as pneumococci, streptococci, or meningococci. The polysaccharide may or may not be medically relevant depending on the use envisioned for the vaccine.

The cytokine can be GM-CSF, IL-3, IFN-γ, or a combination thereof.

This example is not intended to be limiting, and other types of vaccines will be apparent to those skilled in the art from consideration of the specification and practice of the invention.

TABLE II

Vaccine Structure and Components 1. cytokine + antigen (admixed); coadministration in aqueous solution, slow release particles, adjuvants, etc.
2. cytokine + antigen + multivalent carrier; the cytokine, antigen, or both can be directly conjugated to the carrier, i.e.:

3. cytokine-antigen; direct conjugation via covalent bonding
4. cytokine-antigen (covalent bonding) bound to a multivalent carrier, i.e.:

5. cytokine-antigen (fusion protein)
6. cytokine-antigen (fusion protein) bound to a multivalent carrier
7. peptide-cytokine (fusion protein) + antigen
8. peptide-cytokine (fusion protein) + antigen, with the fusion protein, antigen, or both bound to a multivalent carrier
9. cytokine-multivalent carrier, i.e.:

10. antibody complex (i.e., cytokine + cytokine) + antigen
11. antibody complex (i.e., cytokine + cytokine) + antigen + multivalent carrier (the cytokine, antigen, or both can be conjugated to the carrier)
12. anti-cytokine antibody; this is a neutralizing vaccine
13. anti-cytokine antibody + multivalent carrier; this is a neutralizing vaccine
14. Vaccine examples 1 through 13 can be further modified by the addition of CD40L, either admixed or bound to the multivalent carrier
15. Vaccine examples 1 through 14 can be further modified by the addition of one or more cytokines

* * * * *

In sum, the experimental results described above show that B cells activated with a multivalent antigen receptor cross-linker, as for example dextran-conjugated anti-Ig antibody in the experimental model, and either CD40 ligand or LPS, in the presence of the cytokines TGF-β, IL-4, and either IL-5 or IL-2, induce a high rate of IgA class switching. This induction is specifically inhibited by IFN-γ.

Having now fully described the invention, it will be apparent to one of ordinary skill in the art that many changes and modifications can be made thereto without departing from the spirit or scope of the invention as set forth herein. The appended claims are not intended to be limiting.

We claim:

1. A vaccine comprising:
    the antigen of the vaccine in multivalent form;
    at least one cytokine which stimulates IgA class switching; and
    a B cell activator selected from the group consisting of CD40 ligand and LPS, wherein said vaccine stimulates IgA antibody class switching.

2. The vaccine of claim 1, wherein the at least one cytokine is selected from the group consisting of TGF-β, IL-2, IL-4, and IL-5.

3. The vaccine of claim 2 wherein the at least one cytokine is TGF-β.

4. The vaccine of claim 3 further comprising IL-4 and IL-5.

5. The vaccine of claim 3 further comprising IL-4 and IL-2.

6. The vaccine of claim 1 wherein the antigen in multivalent form comprises multiple copies of at least one epitope covalently conjugated to a multivalent carrier selected from the group consisting of dextran and bacterial capsular polysaccharide.

7. The vaccine of claim 6 wherein the multivalent carrier is a bacterial capsular polysaccharide.

8. The vaccine of claim 7 wherein the bacterial capsular polysaccharide is from a bacterium selected from the group consisting of pneumococci, streptococci, and meningococci.

9. The vaccine of claim 6 wherein the at least one cytokine is selected from the group consisting of TGF-β, IL-2, IL-4, and IL-5.

10. The vaccine of claim 9 wherein the at least one cytokine is TGF-β.

11. The vaccine of claim 10 wherein the at least one cytokine additionally comprises IL-4.

12. The vaccine of claim 11 wherein the at least one cytokine additionally comprises IL-2.

13. The vaccine of claim 11 wherein the at least one cytokine additionally comprises IL-5.

* * * * *